(12) United States Patent
Dremin

(10) Patent No.: US 10,660,549 B2
(45) Date of Patent: May 26, 2020

(54) PALM VEIN IMAGING DEVICE

(71) Applicant: OBSCHESTVO S OGRANICHENNOI OTVETSTVENNOSTYU NAUCHNO-ISSLEDOVATELSKY TSENTR "PROSOFT-SISTEMY", Ekaterinburg (RU)

(72) Inventor: Alexandr Vladimirovich Dremin, Ekaterinburg (RU)

(73) Assignee: OBSCHESTVO S OGRANICHENNOI OTVETSTVENNOSTYU "NAUCHNO-ISSLEDOVATELSKY TSENTR PROSOFT-SISTEMY", Ekaterinburg (RU)

( * ) Notice: Subject to any disclaimer, the term of this patent is extended or adjusted under 35 U.S.C. 154(b) by 38 days.

(21) Appl. No.: 15/754,739

(22) PCT Filed: Jul. 3, 2017

(86) PCT No.: PCT/RU2017/050054
§ 371 (c)(1),
(2) Date: Jul. 9, 2018

(87) PCT Pub. No.: WO2018/117912
PCT Pub. Date: Jun. 28, 2018

(65) Prior Publication Data
US 2019/0167159 A1 Jun. 6, 2019

(30) Foreign Application Priority Data
Dec. 23, 2016 (RU) .................... 2016150911

(51) Int. Cl.
*G06K 9/28* (2006.01)
*A61B 5/1172* (2016.01)
(Continued)

(52) U.S. Cl.
CPC .......... *A61B 5/1172* (2013.01); *A61B 5/0064* (2013.01); *A61B 5/117* (2013.01);
(Continued)

(58) Field of Classification Search
CPC ..................... G06K 2009/00932; A61B 5/489
See application file for complete search history.

(56) References Cited

U.S. PATENT DOCUMENTS

2007/0216797 A1* 9/2007 Yoshida ............. G06K 9/00033
348/370
2014/0121637 A1 5/2014 Boyden et al.
(Continued)

FOREIGN PATENT DOCUMENTS

| EP | 2 338 404 | 6/2011 |
| EP | 2 982 301 | 2/2016 |
| EP | 3 007 100 | 4/2016 |

OTHER PUBLICATIONS

International Search Report issued in PCT/RU2017/050054 dated Oct. 19, 2017.

*Primary Examiner* — Brian Werner
(74) *Attorney, Agent, or Firm* — Millman IP Inc.

(57) ABSTRACT

A palm vein imaging device includes a housing, a light sensitive element and an optical imaging system, at least one imaging sensor for capturing images of palm veins, and a controller, wherein the palm vein imaging device contains an infrared transmission filter and a scattering filter installed above the light emitting elements and the light emitting elements are infrared light-emitting diodes emitting light of wavelength of 850 nm and 940 nm. The technical result of the utility model is increased quality of the obtained image of palm vein vascular pattern, reducing the amount of noises
(Continued)

and distortions while imaging and as a result increased reliability of personal identification by means of the claimed device.

8 Claims, 4 Drawing Sheets

(51) Int. Cl.
  *A61B 5/00*    (2006.01)
  *G06K 9/00*    (2006.01)
  *G06K 9/20*    (2006.01)
  *A61B 5/117*   (2016.01)
  *G02B 7/28*    (2006.01)
  *H04N 5/225*   (2006.01)

(52) U.S. Cl.
  CPC .......... *A61B 5/489* (2013.01); *G06K 9/00013* (2013.01); *G06K 9/00033* (2013.01); *G06K 9/2018* (2013.01); *G02B 7/28* (2013.01); *G06K 9/00087* (2013.01); *G06K 2009/00932* (2013.01); *H04N 5/2254* (2013.01)

(56) References Cited

U.S. PATENT DOCUMENTS

| | | | |
|---|---|---|---|
| 2015/0065916 A1* | 3/2015 | Maguire | A61B 17/3403 600/573 |
| 2016/0014308 A1 | 1/2016 | Yamazaki et al. | |
| 2019/0272409 A1* | 9/2019 | Bazrafkan | G06K 9/00026 |

* cited by examiner

PALM VEIN IMAGING DEVICE

This application is the U.S. national phase of International Application No. PCT/RU2017/050054 filed Jul. 3, 2017 which designated the U.S. and claims priority to Russian Patent Application No. 2016150911 filed Dec. 23, 2016, the entire contents of each of which are hereby incorporated by reference.

The present utility model is a biometric device, specifically a device to obtain images of human palm veins. The utility model has application in biometric identification for access control and management, working time tracking, authentication systems used during financial operations, in passport and visa departments, in bank security systems, and so on.

Currently, a number of devices are known that allow to acquire (capture) fingerprints, or scans of the iris for purposes of personal identification. However, personal identification based on palm vein pattern has wider field of application. Vascular pattern of palm veins is unique for each individual and does not change over time. Also, biometric identification by a palm vein pattern does not require direct contact of the hand with the surface of the scanning device which is more hygienic.

The closest known analog is a palm vein imaging apparatus containing a housing with a cover, a sensor, a lens system, a system or infrared light-emitting diodes emitting light of wavelength of 760 nm, and a control system (EP2982301, A61B5/117; G02B7/28; G06K9/00, publ. Oct. 2 2016).

The main drawback of the known device is that it scans the image in the infrared spectrum that is near to the visible spectrum range, 760 nm. Hence, aside from capturing the vascular pattern of palm veins the device also captures the image of palm skin cover in the visible light. The skin cover has lines, cuts, scars that can greatly impair quality of the palm vein image. Such features on the palm skin are not constant over the lifetime and cannot be relied upon to identify a person. Filtering and removing noises while processing palm vein images is a complex task that may lead to errors during mathematical processing of palm vein images and further identification.

A task the present utility model claims to solve is developing a highly reliable and accurate palm vain imaging device that is lack of the above stated drawbacks, and extending the range of available devices of the given purpose.

The technical result of the utility model is increased quality of the obtained image of palm vein vascular pattern, reducing the amount of noises and distortions while imaging and as a result increased reliability of personal identification by means of the claimed device.

The claimed technical result is attributable to the fact that the palm vein imaging device including a housing, a light sensitive element and an optical imaging system, light emitting elements and a control system contains an infrared transmission filter and a scattering filter installed over the light emitting elements, and the light emitting elements are infrared light-emitting diodes emitting light of wavelength of 850 nm and 940 nm.

It is advisable that the device had eight infrared light-emitting diodes with wavelength of 850 nm and eight infrared light-emitting diodes with wavelength of 940 nm.

It is advisable that the light emitting elements were placed around the optical imaging system.

It is advisable that the light-emitting diodes emitting light of wavelengths of 850 nm we placed in between of the light-emitting diodes emitting light of wavelengths of 940 nm.

It is advisable that the control system included at least a central processing unit and a memory.

It is advisable that the infrared transmission filter was at the same time an upper case of the housing.

It is advisable that the device contained printed circuit boards with electronic components placed horizontally in upper and lower parts of the housing and connected with connecting plugs.

It is advisable that the device contained a printed circuit board installed horizontally in the upper part of the housing with light emitting elements and electronic components to control the light emitting elements mounted to it.

It is advisable that the device contained a printed circuit board installed horizontally in the lower part of the housing with at least a light sensitive element, a central processing unit and memory mounted to it.

It is advisable that the device contained a USB interface.

The utility model is illustrated by drawings.

FIG. 1 displays a longitudinal section view of the palm vein imaging device where
1—housing;
2—infrared transmission filter (upper case of the housing);
3—infrared light-emitting diodes of wavelength of 850 nm;
4—infrared light-emitting diodes of wavelength of 940 nm;
5—scattering filter;
6—printed circuit board;
7—printed circuit board;
8—connecting plugs;
9—optical imaging system;
10—light sensitive element;
11—latches;
12—USB connector.

FIG. 2 schematically shows placement of light emitting elements on the printed circuit board of the device.

In the advised variant of design, the palm vein imaging device contains a housing 1 constituting a hollow rectangular box with dimensions of 32×32×30 mm, and an upper rectangular case. The upper case is an infrared transmission filter 2.

In the upper and lower parts of the housing 1 two printed circuit boards 6 and 7 are placed and connected to each other using connecting plugs 8. Placement of electronic components on two printed circuit boards allows to avoid overheating of the device parts.

Figure 3:
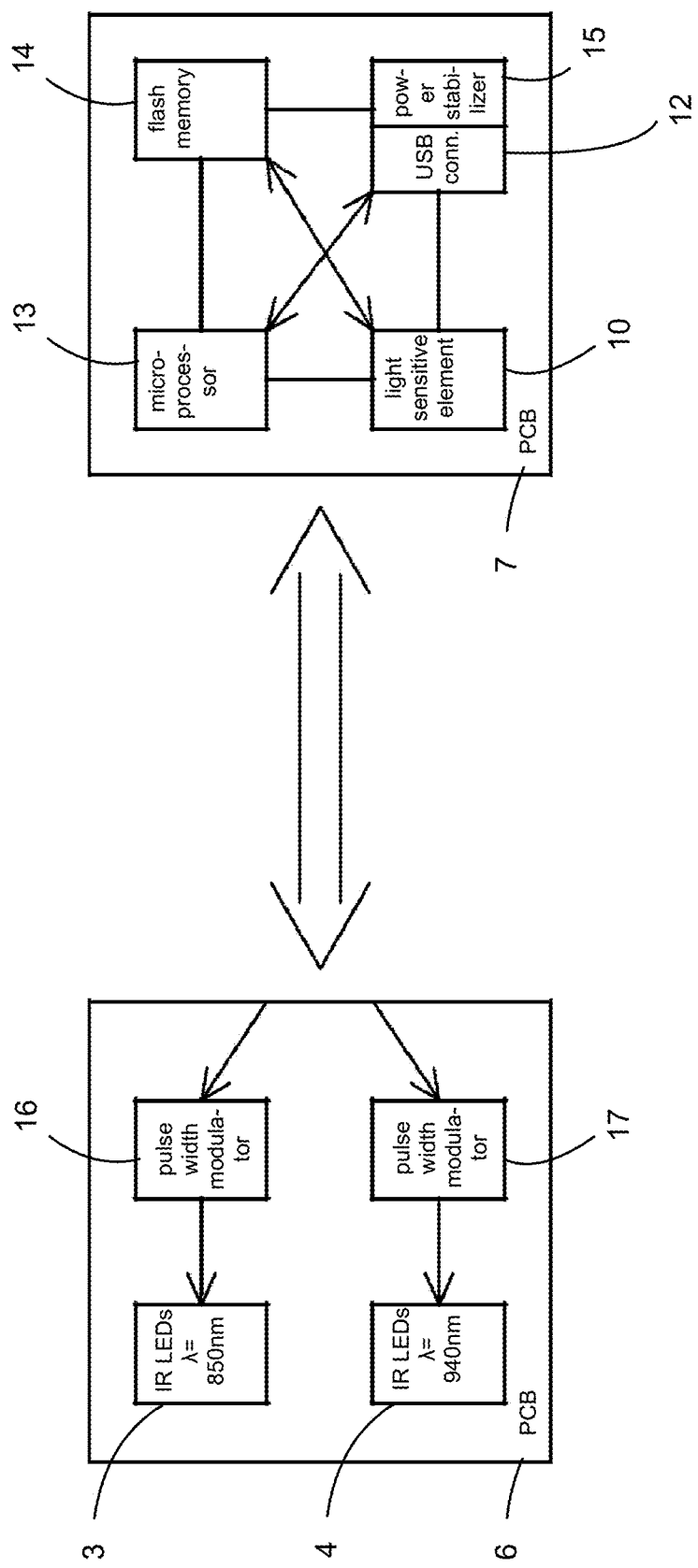
FIG. 3 shows a flow chart of interaction between electronic components of the printed circuit boards, where
13—microprocessor;
14—flash memory;
15—power stabilizer;
16—pulse-width modulator to control infrared light-emitting diodes emitting light of wavelength of 850 nm;
17—pulse-width modulator to control infrared light-emitting diodes emitting light of wavelength of 940 nm.

The lower printed circuit board 7 installed inside the housing 1 using latches 11 contains a RISC microprocessor 13, a flash memory 14, a power stabilizer 15, a USB interface 12 and a light sensitive element 10 (FIG. 3).

The light sensitive element 10 is a CMOS matrix having resolution of 640×480 pixels that provide high quality of palm vein pattern image.

The microprocessor 13 governs acquisition of palm vein images by the CMOS matrix and mathematically processes the acquired image to create a template, further identify and output the identification result to the external control system.

The flash memory 14 stores reference templates that are further used for identification.

The power stabilizer 15 provides the device with DC voltage and filters out power line disturbances.

The USB interface 12 provides communication of the device with external control systems.

Directly above the light sensitive element 10, an optical imaging system 9 constituting a lens is installed. The lens 9 is required to focus the palm image on the CMOS matrix 10 at the distance of 40-60 mm which is the distance between the palm and the device.

Figure 1:
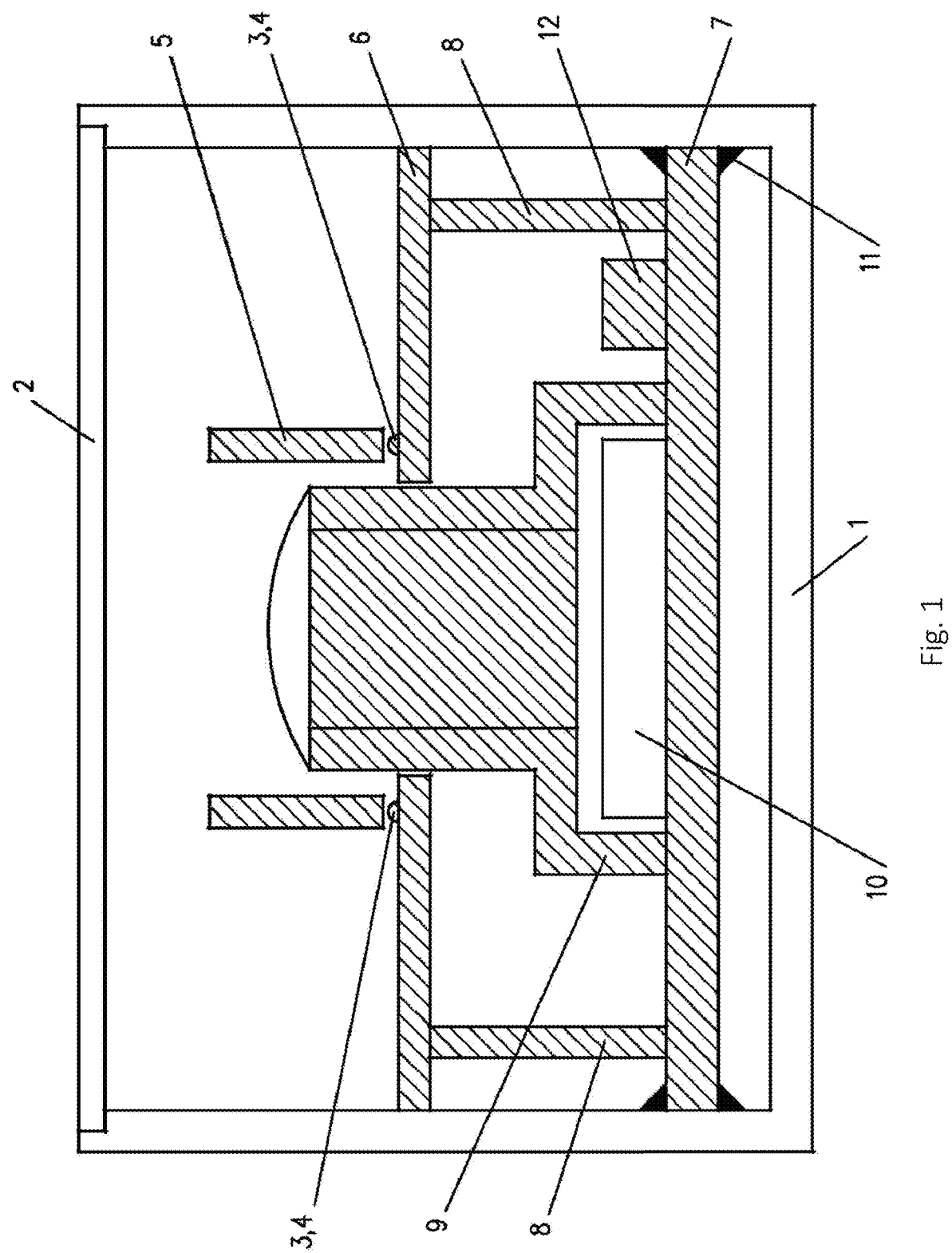
Figure 2:
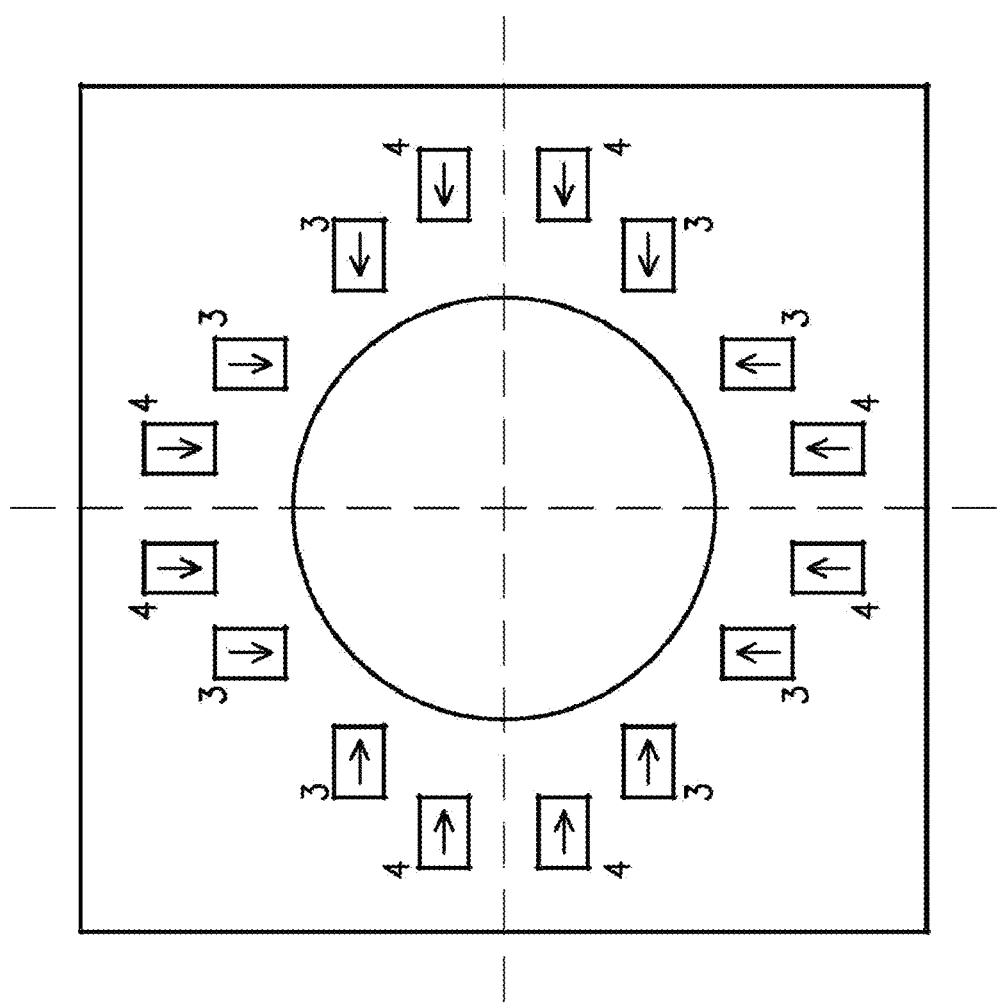

Light emitting elements required to acquire the palm vein image are technically infrared light-emitting diodes emitting light of wavelengths of 850 nm 3 and 940 nm 4. The infrared light-emitting diodes 3 and 4 are mounted on the upper printed circuit board 6 around the lens 9 (FIG. 3). The infrared light-emitting diodes 3 emitting light of wavelength of 850 nm are placed between the infrared light-emitting diodes 4 emitting light of wavelength of 940 nm. On FIG. 2, arrows show the light emission direction of the light-emitting diodes 3 and 4. Such position of the infrared light-emitting diodes provides high quality of the acquired palm vein image.

The infrared light-emitting diodes 3 and 4 are controlled by pulse-width modulators 16 and 17 respectively. The pulse-width modulators 16, 17 are intended to control the infrared light-emitting diodes 3, 4 in impulse mode with pulse relative duration of 10 ms. Such way of light-emitting diode control allows for lower power consumption of the device.

Above the infrared light-emitting diodes 3, 4, a ring-shaped scattering filter 5 is mounted to allow for even lighting of a palm by light-emitting diodes.

The operation principle of the device is based on the fact that reduced hemoglobin in blood vessels absorbs infrared radiation in the spectrum range of 760 to 940 nm. When a palm is exposed to infrared radiation, only blood vessels containing reduced hemoglobin become visible.

The device works in the multispectral mode in infrared ranges of 850 nm and 940 nm and scans a palm vein image using the CMOS matrix and then converts the image into a digital graphic file. Further, the digital data are transmitted to the microprocessor 13 where mathematical processing of the palm vein image is accomplished, specifically: noises are filtered, an area of interest is determined, fixed points and unique features of the blood vessel pattern represented as sections of targeting vectors. Then, located features of the palm vein pattern are saved to a special file—a template. The acquired template is encrypted and is transmitted from the device to an external control system using the USB interface 12.

In the claimed utility model, acquisition of the image is performed in the multispectral mode in infrared ranges of 850 nm and 940 nm. Such approach allows for deep penetration of infrared radiation under the skin of a man, which provides significantly more unique features on the palm vein pattern consequently leading to reduced identification errors. Because the device is capable of acquiring thin blood capillary lying deep under the skin, the resulting image of palm veins is sharp and contains a lot of unique features of blood vessel pattern of palm veins, at the same time the image of the palm print surface is not captured.

Figure 4:
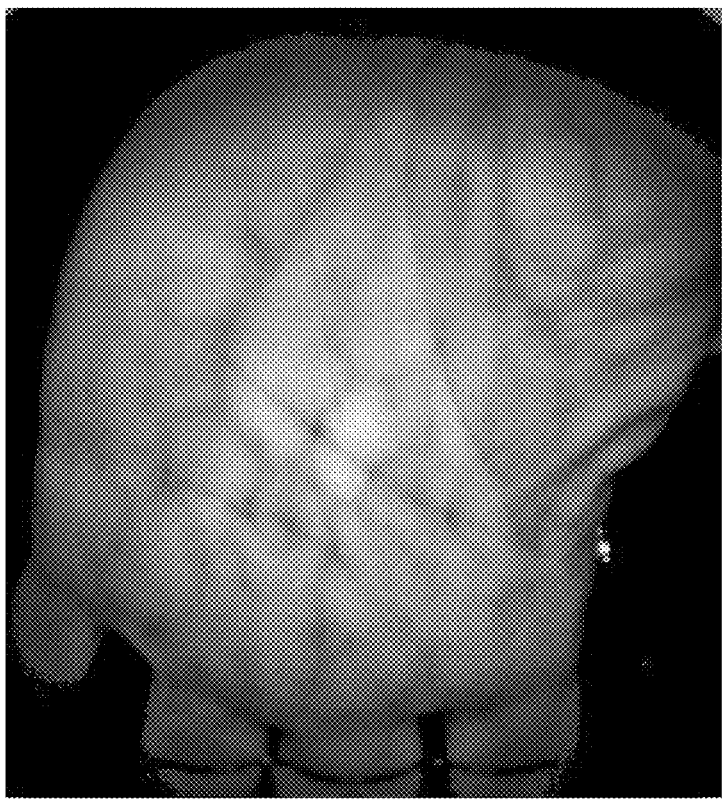
FIG. 4 shows the resulting image captured by the device with an infrared emitter of wavelength of 760 nm, and by the device with infrared emitter of wavelength of 850 nm and 940 nm.
Figure 4:
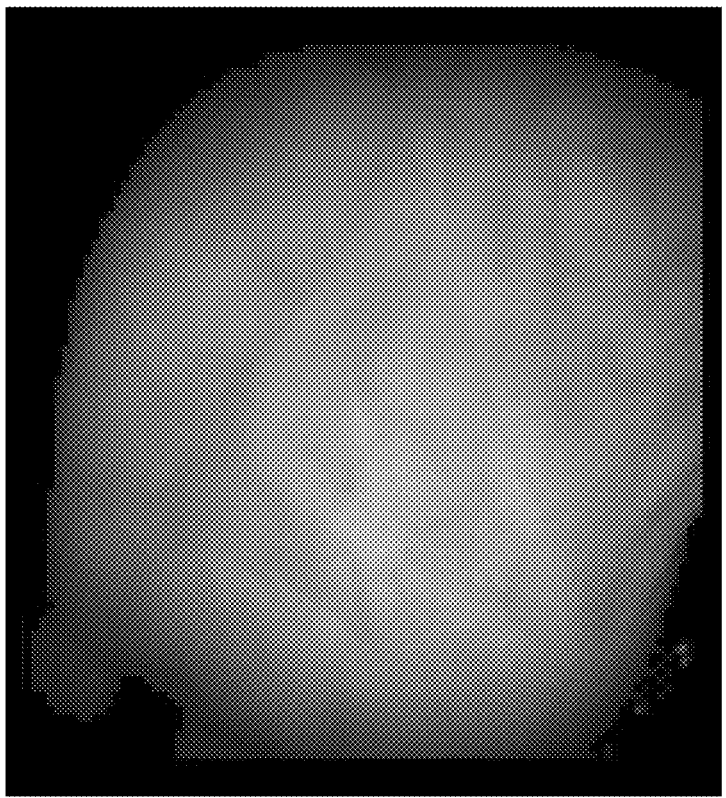

FIG. 4 shows the results of palm vein pattern capture made with two devices. FIG. 4a displays a palm vein image acquired using a device with an infrared emitter of wavelength of 760 nm, and FIG. 4b displays the same palm vein image acquired using a device with infrared emitters of wavelengths of 850 nm and 940 nm (multispectral scan). Analysis of images proves that multispectral scanning allows for higher quality palm vein image capture, because of more unique features of the blood vessel pattern such as thin capillary and less noises and distortions.

The invention claimed is:

1. A palm vein imaging device that includes a housing, at least one imaging sensor for capturing images of palm veins, an optical imaging system, light emitting elements and a controller, wherein the palm vein imaging device contains an infrared transmission filter and a scattering filter installed above the light emitting elements and the light emitting elements are infrared light-emitting diodes emitting light of wavelength of 850 nm and 940 nm, wherein the light-emitting diodes are placed around the optical imaging system so that the light-emitting diodes emitting light of wavelength of 850 nm are placed in between light-emitting diodes emitting light of wavelength of 940 nm.

2. A palm vein imaging device of claim 1, wherein the palm vein imaging device contains eight infrared light-emitting diodes with wavelength of 850 nm and eight infrared light-emitting diodes with wavelength of 940 nm.

3. A palm vein imaging device of claim 1, wherein the controller includes at least a central processing unit and memory.

4. A palm vein imaging device of claim 1, wherein the infrared transmission filter at the same time is an upper case of the housing.

5. A palm vein imaging device of claim 1, wherein the palm vein imaging device contains printed circuit boards installed horizontally in the upper and lower parts of the housing and connected together by means of connecting plugs.

6. A palm vein imaging device of claim 1, wherein the palm vein imaging device contains a printed circuit board installed horizontally in the upper part of the housing with light emitting elements and electronic components to control the light emitting elements mounted to it.

7. A palm vein imaging device of claim 1, wherein the palm vein imaging device contains a printed circuit board installed horizontally in the lower part of the housing with at least the at least one imaging sensor, a central processing unit and memory mounted to it.

8. A palm vein imaging device of claim 1, wherein the palm vein imaging device has a USB interface.

* * * * *